(12) United States Patent
Chou et al.

(10) Patent No.: US 8,517,536 B2
(45) Date of Patent: Aug. 27, 2013

(54) FUNDUS OPTICAL IMAGE DEVICE

(75) Inventors: Chung-Cheng Chou, Luzhu Township, Taoyuan County (TW); William Wang, Taoyuan (TW)

(73) Assignee: Crystalvue Medical Corporation, Guisham Township, Taoyuan County (TW)

( * ) Notice: Subject to any disclaimer, the term of this patent is extended or adjusted under 35 U.S.C. 154(b) by 164 days.

(21) Appl. No.: 13/189,049

(22) Filed: Jul. 22, 2011

(65) Prior Publication Data

US 2012/0026461 A1   Feb. 2, 2012

(30) Foreign Application Priority Data

Jul. 28, 2010  (TW) .............................. 99124979 A

(51) Int. Cl.
  *A61B 3/14*  (2006.01)
  *A61B 3/10*  (2006.01)
(52) U.S. Cl.
  USPC .......................................... 351/206; 351/214

(58) Field of Classification Search
  USPC .................................................. 351/206, 214
  See application file for complete search history.

(56) References Cited

U.S. PATENT DOCUMENTS

| | | | | |
|---|---|---|---|---|
| 2008/0030682 A1* | 2/2008 | Teige et al. | .................... | 351/206 |
| 2008/0079897 A1* | 4/2008 | Goldfain et al. | ............... | 351/205 |
| 2008/0165320 A1* | 7/2008 | Heiberger | ...................... | 351/206 |
| 2008/0278683 A1* | 11/2008 | Su et al. | ......................... | 351/205 |
| 2012/0287255 A1* | 11/2012 | Ignatovich et al. | ............. | 348/78 |
| 2013/0033593 A1* | 2/2013 | Chinnock et al. | ............... | 348/78 |

FOREIGN PATENT DOCUMENTS

| TW | 200630068 A | 9/2006 |
|---|---|---|
| TW | I292048 B | 1/2008 |

\* cited by examiner

*Primary Examiner* — Jordan Schwartz
(74) *Attorney, Agent, or Firm* — Cheng-Ju Chiang

(57) ABSTRACT

A fundus optical image device includes a light source, a first optical element set and a second optical element set. The light emitted from the light source reaches the fundus through the first optical element set. The second optical element set has at least one curvature-adjustable lens. The light emitted from the light source is reflected by the fundus and then passes through the curvature-adjustable lens to present an image of the fundus.

8 Claims, 6 Drawing Sheets

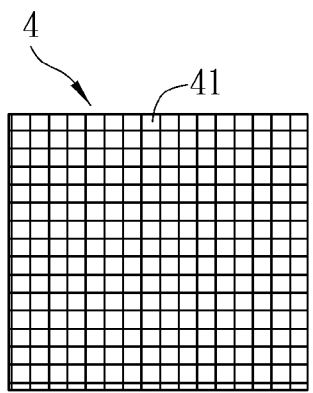
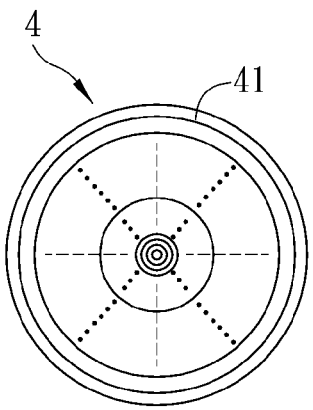
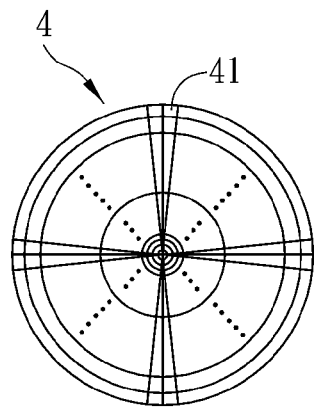
FIG. 7A      FIG. 7B      FIG. 7C
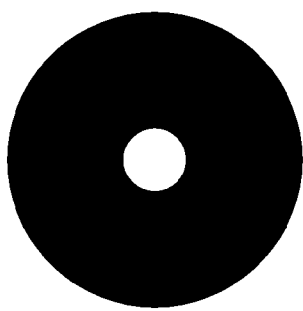
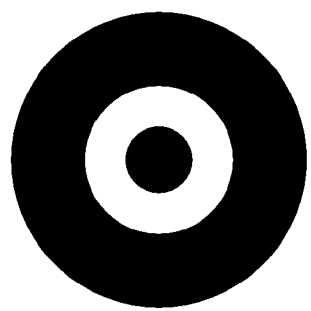
FIG. 8A      FIG. 8B

FUNDUS OPTICAL IMAGE DEVICE

CROSS REFERENCE TO RELATED APPLICATIONS

This Non-provisional application claims priority under 35 U.S.C. §119(a) on Patent Application No(s). 099124979 filed in Taiwan, Republic of China on Jul. 28, 2010, the entire contents of which are hereby incorporated by reference.

BACKGROUND OF THE INVENTION

1. Field of Invention

The present invention relates to an optical inspection device and, in particular, to an optical image inspection device for eyes.

2. Related Art

The common eye inspection device includes the pneumatic tonometer, kerato-refractometer, fundus optical image device, and the likes. In particular, the fundus optical image device is an optical inspection device for observing the fundus.

The fundus optical image device is mainly used to inspect the pathological changes of the macula lutea and the optic nerve of the retina. It can be directly applied to inspect the fundus without administering the mydriatic eye drops to the eyes. Thus, the fundus optical image device can provide the simple, fast, precise and cheap inspection. Moreover, through the fundus optical image device, some fundus pathological changes, such as glaucoma, neuropapillitis, or macular degeneration, can be inspected out.

In addition, since the fundus inspection can directly observe the blood vessels, the fundus optical image device can further inspect some other symptoms such as diabetes retinopathy.

As shown in FIG. 1, a conventional fundus optical image device 1 mainly includes a light unit 11, a light-path unit 12, an image capturing unit 13 and an observation unit 14. The light unit 11 includes an optical lens set for directing a light emitted by a light source to the fundus 21 of an eye 2. Then, the light reflected by the fundus 21 enters the light-path unit 12 for presenting the image of the fundus 21, and the image capturing unit 13 captures the image. After that, the user can observe the image of the fundus 21 and/or adjust the resolution thereof by the observation unit 14.

As mentioned above, the light-path unit 12 of the conventional fundus optical image device 1 must have a position-adjustable lens for various fundi that have different focuses. Thus, the light-path unit 12 also needs to configure a space for moving the position-adjustable lens, so that the dimension of the fundus optical image device 1 can not be further minimized. Besides, this feature also causes the complexity of the assembling procedure.

Therefore, it is an important subject of the invention to provide a fundus optical image device with more compact dimension.

SUMMARY OF THE INVENTION

To achieve the foregoing subject, an objective of the present invention is to provide a fundus optical image device with more compact dimension.

To achieve the above objective, the present invention discloses a fundus optical image device, which includes a light source, a first optical element set and a second optical element set. The light source emits a light, and the light emitted from the light source reaches a fundus through the first optical element set. The second optical element set includes at least one curvature-adjustable lens. The light emitted from the light source is reflected by the fundus and then passes through the curvature-adjustable lens to present an image of the fundus.

In one embodiment of the invention, the curvature-adjustable lens is an electrowetting curvature lens or a dielectrophoresis curvature lens.

In one embodiment of the invention, the first optical element set includes at least a lens, a first diaphragm and a spectroscope. The light emitted from the light source passes through the lens, the first diaphragm and the spectroscope in order, and then reaches the fundus. For example, the first diaphragm includes an annular opening, and it is an electrowetting microarray diaphragm or a dielectrophoresis microarray diaphragm.

In one embodiment of the invention, the second optical element set further includes a second diaphragm and a lens. For example, the second diaphragm has a central opening, and it is an electrowetting microarray diaphragm or a dielectrophoresis microarray diaphragm.

In one embodiment of the invention, the second diaphragm is disposed between the curvature-adjustable lens and the fundus, the lens cooperates with the curvature-adjustable lens, and the curvature-adjustable lens is disposed between the second diaphragm and the lens. Alternatively, the second diaphragm is disposed between the curvature-adjustable lens and the fundus, and the lens cooperates with the curvature-adjustable lens and is disposed between the second diaphragm and the curvature-adjustable lens.

In one embodiment of the invention, the fundus optical image device further includes an observation module for observing the image of the fundus through the curvature-adjustable lens. Moreover, the fundus optical image device further includes an image capturing module for capturing the image of the fundus through the curvature-adjustable lens.

As mentioned above, the fundus optical image device of the present invention has a curvature-adjustable lens, which can adjust the curvature itself for fitting the pupils of different eyes, for changing the light paths. Thus, the conventional lens needed extra space for movement can be substituted by the curvature-adjustable lens of the invention, so that the dimension of the fundus optical image device can be minimized.

BRIEF DESCRIPTION OF THE DRAWINGS

The invention will become more fully understood from the detailed description and accompanying drawings, which are given for illustration only, and thus are not limitative of the present invention, and wherein:

FIGS. 7A to 7C are schematic diagrams showing the microarray diaphragm;

FIG. 8A is a schematic diagram showing a second diaphragm; and

FIG. 8B is a schematic diagram showing a first diaphragm.

DETAILED DESCRIPTION OF THE INVENTION

The present invention will be apparent from the following detailed description, which proceeds with reference to the accompanying drawings, wherein the same references relate to the same elements.

Figure 1:
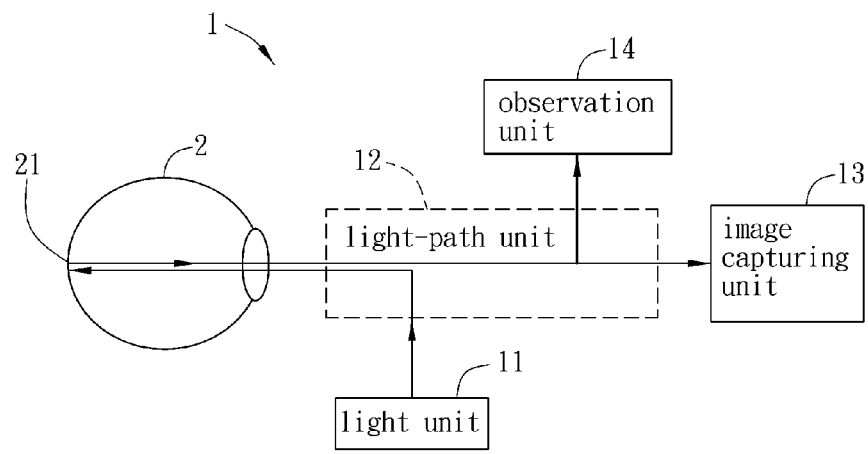
FIG. 1 is a schematic diagram showing a conventional fundus optical image device.
Figure 2:
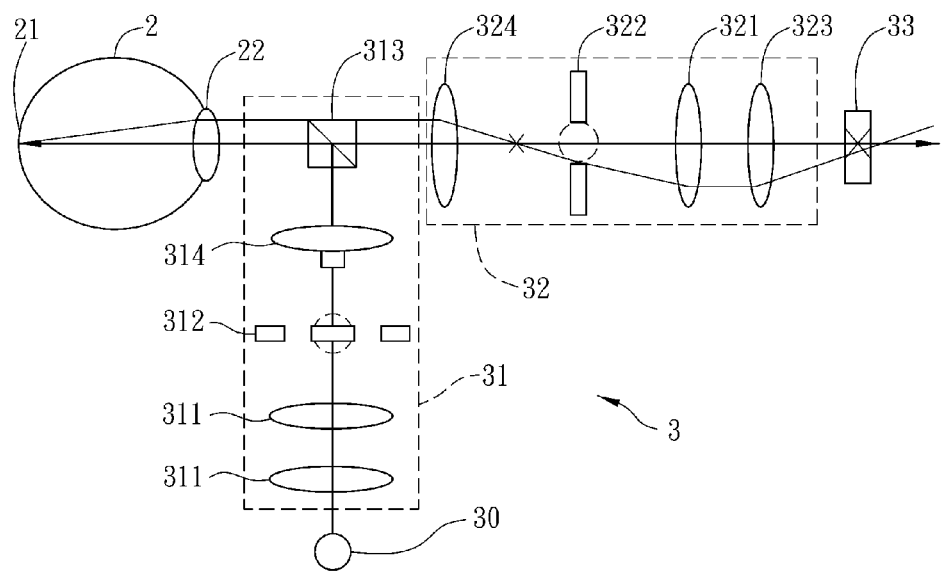
FIG. 2 is a schematic diagram showing a fundus optical image device according to a preferred embodiment of the invention.

With reference to FIG. 2, a fundus optical image device 3 for inspecting a fundus 21 includes a light source 30, a first optical element set 31, and a second optical element set 32. The light source 30 emits a light, and the light emitted from the light source 30 reaches the fundus 21 of an eye 2 through the first optical element set 31. The second optical element set 32 includes at least one curvature-adjustable lens 321. The light emitted from the light source 30 is reflected by the fundus 21 and then passes through the curvature-adjustable lens 321 to present an image of the fundus 21.

In this embodiment, the first optical element set 31 includes at least one lens 311, a first diaphragm 312, a spectroscope 313 and a lens 314. The second optical element set 32 further includes a second diaphragm 322 and a lens 323. The second diaphragm 322 is disposed between the curvature-adjustable lens 321 and the fundus 21. The lens 323 cooperates with the curvature-adjustable lens 321. The curvature-adjustable lens 321 is disposed between the second diaphragm 322 and the lens 323.

The first diaphragm 312 includes an annular opening, and the second diaphragm 322 has a central opening. Thus, the light path traveling to the fundus 21 and the light path reflected from the fundus 21 are not overlapped.

The light emitted from the light source 30 passes through the lens 311, the first diaphragm 312, the spectroscope 313 and the pupil 22 of the eye 2 in order, and then reaches the fundus 21 of the eye 2. In addition, the light reflected by the fundus 21 passes through the pupil 22, the spectroscope 313, the lens 324, the second diaphragm 322, the curvature-adjustable lens 321 and the lens 323 in order, thereby presenting the image of the fundus 21.

Besides, the fundus optical image device 3 further includes an image capturing module 33 for capturing the image of the fundus 21 through the curvature-adjustable lens 321.

Moreover, the fundus optical image device 3 may further include an observation module for observing the image of the fundus through the curvature-adjustable lens. The observation module can be disposed at the location of the image capturing module 33.

Figure 3:
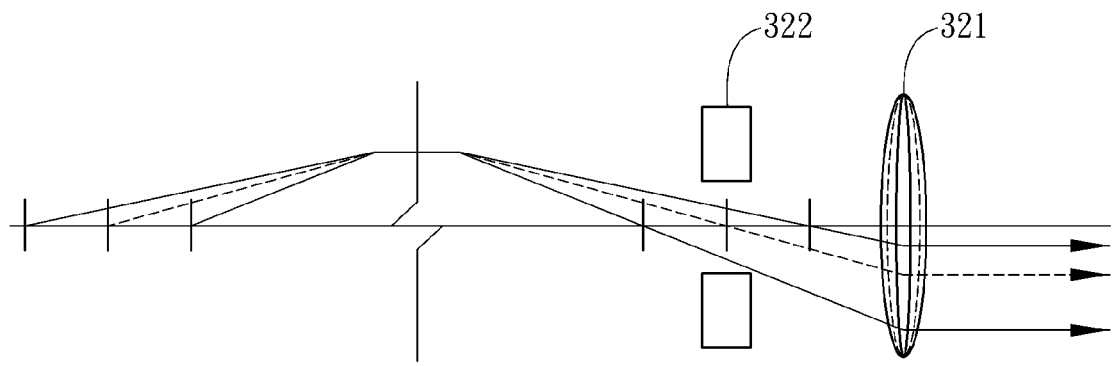
FIG. 3 is a schematic diagram of the curvature-adjustable lens of FIG. 2.

Referring to FIG. 3, the focus of the curvature-adjustable lens 321 can be adjusted for altering the light path, so that the second optical element set 32 can adapt to various eye curvatures of different persons, which may be caused by different near visions for example. In addition, the curvature-adjustable lens 321 can alter the light path without moving its position, so that the entire fundus optical image device 3 can be made more compact.

Figure 4A:
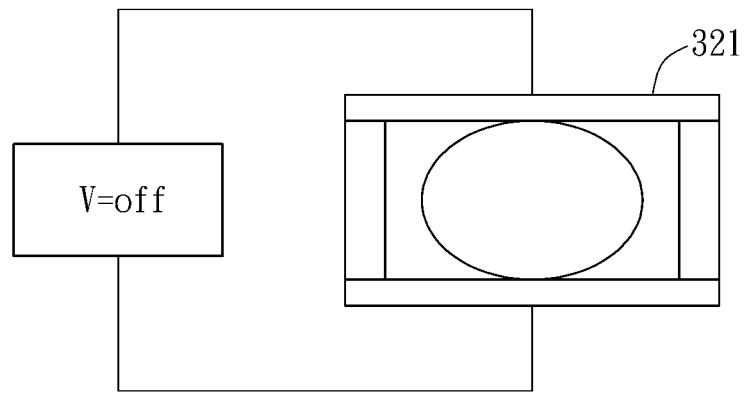
FIG. 4A and FIG. 4B are schematic diagrams showing the operations of the curvature-adjustable lens of FIG. 2.
Figure 4B:
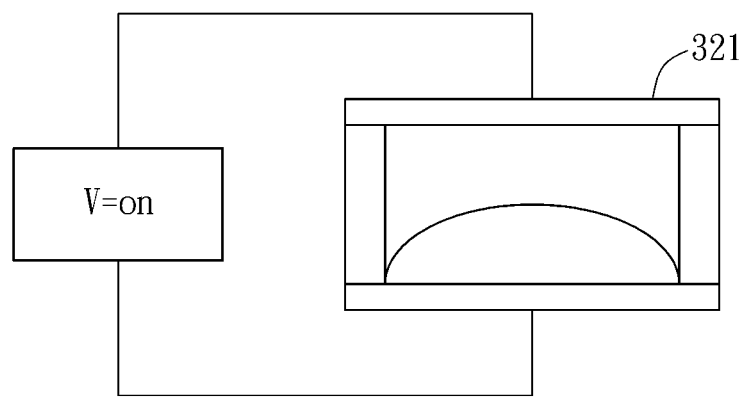

With reference to FIGS. 4A and 4B, in one embodiment of the invention, the curvature-adjustable lens 321 is an electrowetting curvature lens.

The electrowetting curvature lens utilizes the liquid for altering its focus, so it has the advantages of high performance, low cost, compact, and low power consumption. This technique mainly uses the property of the electro-conductive aqueous liquid and the nonconductive oil. When using these two kinds of liquids to construct the lens structure, the contact area between the aqueous liquid and the oil can be altered by applying different currents. Accordingly, the expansion of the contact area allows the increase of the curvature, so that the focus can be moved similar to the focusing operation.

The electrowetting curvature lens includes two conductive layers and an isolation layer for separating the two conductive layers. The conductive layers are made of the transparent conductive material such as ITO. The conductive layers and isolation layer form a space for accommodating the liquids. In practice, when applying voltage to the conductive layers, the curvature of the liquids can be altered due to the difference of the conductivity, so that the focus of the lens can be changed.

For example, as shown in FIG. 4A, when the voltage is not applied, the liquid inside the lens does not have substantially change. As shown in FIG. 4B, when the voltage is applied, the liquid inside the lens becomes flatter. In brief, the curvature of the curvature-adjustable lens 321 can be altered by whether to apply the voltage or not.

Alternatively, the curvature-adjustable lens may be a dielectrophoresis curvature lens. In the dielectrophoresis curvature lens, the electrical couples induced by the external electric field and the interaction of the external electric field can drive the particles. Thus, the particles do not need to carry electricity, and they can be driven by the dielectrophoresis force by applying alternating voltage.

Figure 5:
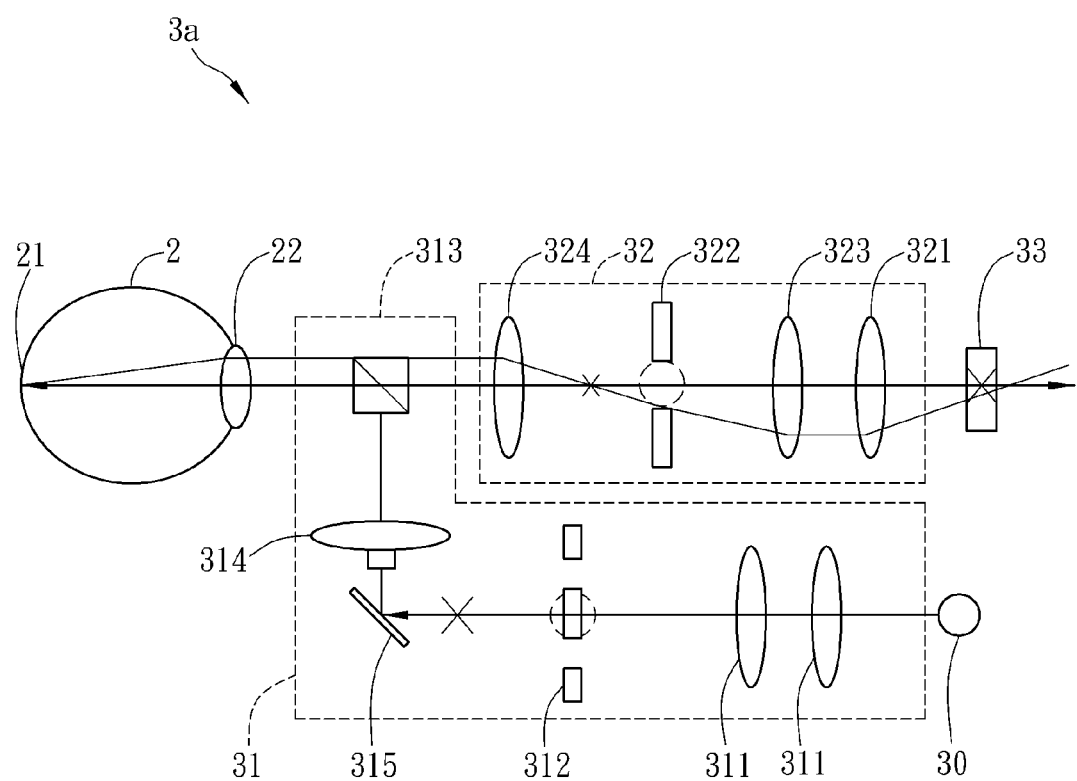
FIG. 5 is a schematic diagram showing a fundus optical image device according to another preferred embodiment of the invention.

Referring to FIG. 5, a fundus optical image device 3a of another embodiment is different from the previous embodiment in that the first optical element set 31 further includes a reflective mirror 315. The light emitted from the light source 30 passes through the lens 311, the first diaphragm 312, the reflective mirror 315, the lens 314, the spectroscope 313 and the pupil 22 of the eye 2 in order, and then reaches the fundus 21 of the eye 2. In addition, the light reflected by the fundus 21 passes through the pupil 22, the spectroscope 313, the lens 324, the second diaphragm 322, the curvature-adjustable lens 321 and the lens 323 in order, thereby presenting the image of the fundus 21.

Figure 6A:
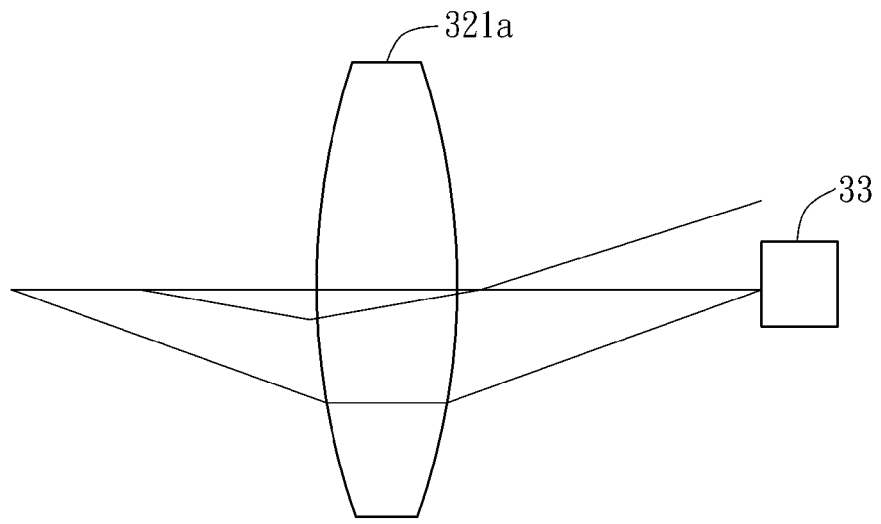
FIGS. 6A and 6B are schematic diagrams of the curvature-adjustable lens of a fundus optical image device according to another preferred embodiment of the invention.
Figure 6B:
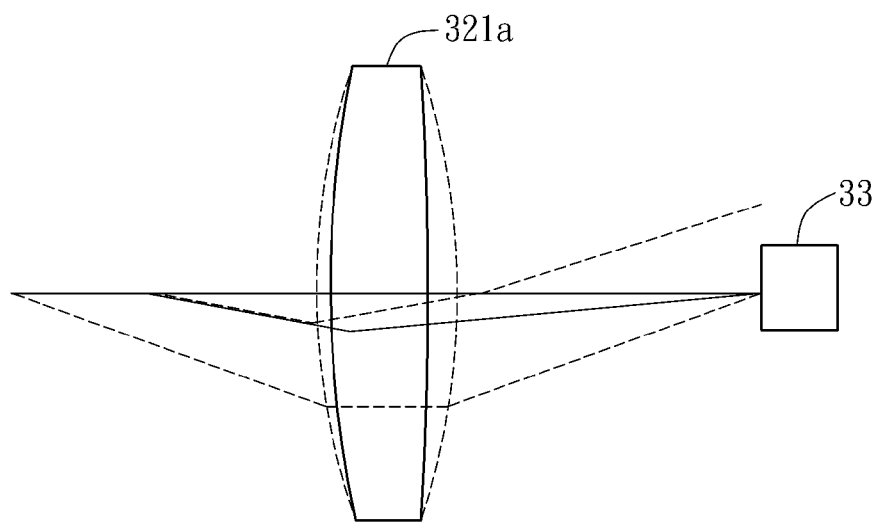

Referring to FIGS. 6A and 6B, this aspect is different from the previous embodiment in that the curvature-adjustable lens 321 and the lens 323 are integrated as a curvature-adjustable lens 321a. The curvature-adjustable lens 321a is a biconvex lens, which can generate a larger refraction angle.

Besides, in the above-mentioned embodiments, the first or second diaphragm may also be an electrowetting microarray diaphragm or a dielectrophoresis microarray diaphragm.

Reference to FIGS. 7A to 7C, a microarray diaphragm 4 includes a plurality of switch units 41, which are arranged in a two-dimensional array as shown in FIG. 7A, in an annular shape as shown in FIG. 7B, or in an arc shape as shown in FIG. 7C. The microarray diaphragm 4 can substitute for the first or second diaphragm of any of the previous embodiments.

In the microarray diaphragm 4, the switch units 41 are respectively controlled by, for example, the voltage signals. The Switch units 41 can be made by electrochromic materials. The electrochromic is the procedure of applying a voltage differential to the material so that the material can be transformed from the original transparent state to the colorful state. The electrochromic material is usually colorless while not applying any voltage to it, and is colorful while applying voltage to it. For example, when a positive voltage is applied to the electrochromic material, it can be transformed from the original colorless to the color of deep blue. If the voltage is reversed, the electrochromic material can be transformed from the color of deep blue back to the colorless. This embodiment is to applying different voltages to the switch units 41 for changing the transmittance, so that the microarray diaphragm 4 can have a changeable light penetrable area.

Alternatively, the microarray diaphragm 4 may also be made of liquid crystal materials. By using voltages to control the rotation of the liquid crystal, switch units 41 can present different transmittances. Thus, the microarray diaphragm 4 can have a changeable light penetrable area.

Besides, the switch units 41 of the microarray diaphragm 4 may be made of the electrowetting material or dielectrophoresis material. The electrowetting material utilizes the liquid for altering its focus, so that it has the advantages of high performance, low cost, compact, and low power consumption. This technique mainly uses the property of the electro-conductive aqueous liquid and the nonconductive oil. When using these two kinds of liquids to construct the lens structure, the contact area between the aqueous liquid and the oil can be altered by applying different currents. Accordingly, the expansion of the contact area allows the increase of the curvature, so that the focus can be moved similar to the focusing operation. The switch unit 41 can alter its focus to control whether to permit the light passing through it to enter the next component.

Alternatively, the switch unit 41 may be made of the dielectrophoresis material. In the dielectrophoresis material, the electrical couples induced by the external electric field and the interaction of the external electric field can drive the particles. Thus, the particles do not need to carry electricity, and they can be driven by the dielectrophoresis force by applying alternating voltage.

For example, in the second diaphragm made of microarray diaphragm, the switch units of the microarray diaphragm are controlled by the voltage signals so as to present the annular light penetrable area and the center light non-penetrable area as shown in FIGS. 4A and 8A.

Besides, in the first diaphragm made of microarray diaphragm, the switch units of the microarray diaphragm are controlled by the voltage signals so as to present the center light penetrable area as shown in FIGS. 4B and 8B.

In summary, the fundus optical image device of the present invention has a curvature-adjustable lens, which can adjust the curvature itself for fitting the pupils of different eyes, for changing the light paths. Thus, the conventional lens needed extra space for movement can be substituted by the curvature-adjustable lens of the invention, so that the dimension of the fundus optical image device can be minimized.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. A fundus optical image device, comprising:
    a light source emitting a light;
    a first optical element set, wherein the first optical element set comprises a first lens, a first diaphragm and a spectroscope, and the light emitted from the light source passes through the first lens, the first diaphragm and the spectroscope in order, and then reaches the fundus; and
    a second optical element set comprising a second lens, a second diaphragm and a third lens, wherein the second diaphragm is disposed between the second lens and the fundus, the third lens is cooperated with the second lens, and the second lens is disposed between the second diaphragm and the third lens, wherein the light emitted from the light source is reflected by the fundus and then passes through the second lens to present an image of the fundus, and the second diaphragm is an electrowetting microarray diaphragm or a dielectrophoresis microarray diaphragm.

2. The fundus optical image device according to claim 1, wherein the second lens is an electrowetting curvature lens or a dielectrophoresis curvature lens.

3. The fundus optical image device according to claim 1, wherein the first diaphragm comprises an annular opening.

4. The fundus optical image device according to claim 1, wherein the first diaphragm is an electrowetting microarray diaphragm or a dielectrophoresis microarray diaphragm.

5. The fundus optical image device according to claim 1, wherein the second optical element set further comprises:
    a fourth lens cooperating with the second lens, wherein the fourth lens is disposed between the second diaphragm and the fundus.

6. The fundus optical image device according to claim 1, wherein the second diaphragm has a central opening.

7. The fundus optical image device according to claim 1, further comprising:
    an observation module for observing the image of the fundus through the second lens.

8. The fundus optical image device according to claim 1, further comprising:
    an image capturing module for capturing the image of the fundus through the second lens.

* * * * *